(12) United States Patent
Kim et al.

(10) Patent No.: US 9,457,104 B2
(45) Date of Patent: *Oct. 4, 2016

(54) HYDROPHILIC NANOPARTICLES SURFACE-MODIFIED WITH MONOSACCHARIDE PHOSPHATE OR MONOSACCHARIDE PHOSPHATE DERIVATIVES, ITS COLLOIDAL SOLUTION AND USE THEREOF

(75) Inventors: Eung Gyu Kim, Daejeon (KR); Bong-Sik Jeon, Daejeon (KR); Eun Byul Kwon, Daejeon (KR); Ju Young Park, Daejeon (KR); Wan Jae Myeong, Daejeon (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/236,502

(22) PCT Filed: Aug. 3, 2012

(86) PCT No.: PCT/KR2012/006206
§ 371 (c)(1),
(2), (4) Date: Jan. 31, 2014

(87) PCT Pub. No.: WO2013/019090
PCT Pub. Date: Feb. 7, 2013

(65) Prior Publication Data
US 2014/0161734 A1 Jun. 12, 2014

(30) Foreign Application Priority Data
Aug. 3, 2011 (KR) ........................ 10-2011-0077534

(51) Int. Cl.
| | | |
|---|---|---|
| *A61B 5/055* | (2006.01) | |
| *A61K 9/16* | (2006.01) | |
| *A61K 49/18* | (2006.01) | |
| *A61K 47/26* | (2006.01) | |
| *A61K 9/51* | (2006.01) | |
| *A61K 9/50* | (2006.01) | |

(52) U.S. Cl.
CPC ......... *A61K 49/1824* (2013.01); *A61K 9/5036* (2013.01); *A61K 9/5115* (2013.01); *A61K 47/26* (2013.01); *A61K 49/1845* (2013.01); *A61B 5/055* (2013.01)

(58) Field of Classification Search
CPC ............. A61K 49/18; A61K 49/1821; A61K 49/1827; A61K 49/183; A61K 49/1833; A61K 49/1836; A61K 49/1839; A61K 49/1845; A61K 49/1842
USPC ...................... 424/465–468, 9.323
See application file for complete search history.

(56) References Cited

U.S. PATENT DOCUMENTS

| | | | |
|---|---|---|---|
| 5,160,725 A | 11/1992 | Pilgrimm | |
| 7,780,953 B2 | 8/2010 | Port et al. | |
| 2003/0147858 A1* | 8/2003 | Renaud ................ | A61K 35/742 424/93.4 |
| 2003/0147958 A1* | 8/2003 | Ahn et al. ..................... | 424/486 |
| 2004/0253181 A1 | 12/2004 | Port et al. | |
| 2007/0128117 A1* | 6/2007 | Bettinger ............. | A61K 49/223 424/9.52 |
| 2009/0309597 A1* | 12/2009 | Horak ................ | A61K 49/1836 324/318 |
| 2009/0324494 A1 | 12/2009 | Ham et al. | |
| 2010/0143263 A1 | 6/2010 | Cheon et al. | |
| 2010/0297025 A1 | 11/2010 | Port et al. | |
| 2011/0020243 A1* | 1/2011 | Aydogan ............ | A61K 31/7004 424/9.42 |
| 2011/0105825 A1* | 5/2011 | Nayfach-Battilana | A61K 41/0052 600/12 |
| 2011/0165086 A1 | 7/2011 | Lee et al. | |
| 2013/0045160 A1 | 2/2013 | Ham et al. | |

FOREIGN PATENT DOCUMENTS

| | | |
|---|---|---|
| JP | 2663976 B2 | 6/1997 |
| JP | 2013-514123 A | 4/2013 |
| KR | 10-2010-0038583 | 12/2009 |
| WO | 2007/097593 A1 | 8/2007 |
| WO | 2009-136763 | 11/2009 |
| WO | 2012018240 A2 | 2/2012 |

OTHER PUBLICATIONS

Yong Il Park et al: 11 Transformation of hydrophobic iron oxide nanoparticles to hydrophilic and biocompatible maghemite nanocrystals for use as highly efficient MRI contrast agent , Journal of Materials Chemistry, vol. 21, No. 31, Mar. 16, 2011, p. 11472.
European Search Report for corresponding European Patent Application No. 11814840.2, dated Mar. 18, 2015.

(Continued)

Primary Examiner — Micah-Paul Young
(74) Attorney, Agent, or Firm — Hauptman Ham, LLP

(57) ABSTRACT

Disclosed are a composition including hydrophilic nanoparticles that have a monosaccharide-phosphate or a derivative thereof adhered to the surface thereof, a colloidal solution of the composition dispersed in water, and a magnetic resonance imaging contrast agent including the colloidal solution. According to the present invention, nanoparticles having biocompatibility and excellent water-dispersibility can be prepared by modifying the surface of inorganic nanoparticles. The prepared nanoparticles may be effectively used in a variety of applications including, for example, in vivo imaging applications such as an MRI contrast agent, nano-electronic convergence technologies such as a quantum dot light emitting device, biomedical applications such as hyperthermia, or the like. Moreover, compared to existing nanoparticles dispersed by a dispersion stabilizer known in the art, excellent dispersion stability and a relatively small hydrodynamic diameter may be attained.

10 Claims, 7 Drawing Sheets

(56) References Cited

OTHER PUBLICATIONS

International Search Report for corresponding PCT application No. PCT/KR2012/006206.
H.B. Na, et al., "Versatile PEG-derivatized phosphine oxide ligands for waterdispersible metal oxide nanocrystals," Chemical Communications, pp. 5167-5169, 2007, <www.rsc.org/chemcomm>.
Shouheng Sun et al., "Size-Controlled Synthesis of Magnetite Nanoparticles," J. Am. Chem Soc., 2002, IBM T. J. Watson Research Center, Yorktown Heights, New York, p. 8204-8205, vol. 124.
Jongnam Park et al., "Ultra-large-scale Syntheses of Monodisperse Nanocrystals," Nature Materials, 2004, Seoul, Korea, p. 891-895, vol. 3.

* cited by examiner

1: Glucose 6 phosphate-3nm : 3.8nm   2: Mannose 6 phosphate-7nm: 8.7nm
3: Fructose 6 phosphate-10nm : 11.3nm

HYDROPHILIC NANOPARTICLES SURFACE-MODIFIED WITH MONOSACCHARIDE PHOSPHATE OR MONOSACCHARIDE PHOSPHATE DERIVATIVES, ITS COLLOIDAL SOLUTION AND USE THEREOF

TECHNICAL FIELD

The following disclosure relates to a composition including hydrophilic nanoparticles having a monosaccharide-phosphate or its derivative bonded on the surface thereof, a colloidal solution thereof and its use. More particularly, a composition including inorganic nanoparticles surface-modified with a monosaccharide-phosphate or its derivative, a colloidal solution prepared by dispersing the composition in water, and a magnetic resonance imaging contrast agent including the same.

BACKGROUND ART

Nanoparticles are used in a broad range of applications such as in vivo imaging technology, medical applications, gene transfer, drug delivery, diagnosis and treatment of diseases, etc. Specifically, nanoparticles are widely used in a variety of biomedical applications including, for example, a magnetic resonance imaging (MRI) contrast agent, cellular level therapy, hyperthermia, drug delivery, nucleic acid isolation, or the like, thereby increasing importance thereof.

The most important requirement for the application of nanoparticles in biomedical applications is primarily to ensure high quality nanoparticles and, in addition, to allow nanoparticles to have water-dispersion stability to stably maintain the nanoparticles in vivo. Here, a high quality nanoparticle may mean a nanoparticle with features of; (i) uniformity of particle size, (ii) easy control of particle size, (iii) excellent particle crystallinity, etc.

In order to accomplish satisfactory results in vitro and in vivo by applying such high quality nanoparticles to a human body and bioscience technologies, it is necessary to select a nanoparticle suitable to the characteristics of a specific application and, above all, a skill to treat nanoparticles with a bio-compatible material having excellent dispersibility.

Nanoparticles commercially available in the art are mostly synthesized by co-precipitation that controls pH in an aqueous system to precipitate the nanoparticles, or obtained by synthesis in a gas phase. However, nanoparticles generated by the foregoing processes are significantly agglomerated due to the lack of a stabilizer on the surface of the synthesized nanoparticles, and have difficulties in controlling a size of nanoparticle and preparing nanoparticles with a uniform size.

A method for synthesis of nanoparticles having a lipophilic surfactant adhered to the surface thereof by thermal decomposition of an inorganic precursor as well as the surfactant in an organic solvent at high temperature has recently been developed. This method has advantages in that size and shape of nanoparticles are preferably controlled, the synthesized nanoparticles show high uniformity in size and excellent crystallinity without agglomeration. However, the synthesized nanoparticles also have disadvantages in that, since a surfactant having hydrophobic properties is adhered the surface of the synthesized nanoparticles, these nanoparticles are not dispersed in water and are problematic when used in vivo. Therefore, in order to use such prepared inorganic nanoparticles in vivo, surface modification into a hydrophilic state is necessary. There are generally three kinds of methods for surface modification of hydrophobic nanoparticles into a hydrophilic state.

A first one is a ligand exchange method, wherein excess of ligands having functional groups bondable to the surface of nanoparticles are introduced to allow the ligands to be bonded at a site where the surfactant was detached.

A second one is an encapsulation method, wherein amphiphilic ligands are introduced to nanoparticles, in order to allow a hydrophobic portion of the amphiphilic ligand facing a surfactant part of the nanoparticle while a hydrophilic portion thereof is exposed to the outside, thus becoming hydrophilic. However, this method requires complicated experimental conditions since separate particles are surrounded with an amphiphilic material, and causes problems for mass production.

A third one is a method of using micelles wherein micelles are prepared in a solvent containing hydrophobic nanoparticles dispersed therein and the nanoparticles are introduced into the micelles. This method is characterized in that several nanoparticles are introduced into one micelle, thus causing a problem in preparing hydrophilic nanoparticles having a small hydrodynamic diameter. Moreover, a problem of causing breakage of micelles due to increase/decrease in a concentration of ions in vivo and/or a blood flow rate may be caused.

Accordingly, numerous studies have currently been executed to develop a novel method for hydrophilization of nanoparticles through ligand exchanging. However, it is important to suitably select a functional group enabling bonding of the ligand to the surface of nanoparticle that is combined with a surfactant. A chargeable functional group can generally bond well to the surface of a nanoparticle and examples thereof may mostly include amines, phosphates, sulfates, carboxylate, etc.

In general, hydrophilized nanoparticles may have dispersion stability in water depending upon characteristics of hydrophilic materials. In the case of a single molecule, nanoparticles are not cohered due to repulsion caused by charge of molecules, instead, maintain water-dispersibility. However, the nanoparticles may be cohered with a change of pH, thus having inferior dispersion stability in vivo. Therefore, hydrophilization of nanoparticles including surface modification using ligands with relatively large molecular weight and utilizing van-der-Waals force has currently been studied. However, the nanoparticles hydrophilized by ligands having a large molecular weight entail problems such as a large hydrodynamic diameter and difficulties in ligand exchanging when the molecular weight is increased.

Moreover, preparation of bio-compatible ligands needs a complicated manufacturing process and entails a difficulty in mass production thereof.

In recent years, a water dispersion method of nanoparticles using a polymer comprising of phosphine oxide and polyethyleneglycol (PEG) has been disclosed in, for example, "Versatile PEG-derivatized Phosphine Oxide Ligands for Water-Dispersible Metal Oxide Nanocrystals," by Hyon Bin Na, In Su Lee, Heon Jin Seo, Yong Il Park, Jung Hee LEE, Sang Wook Kim and Taeghwan Hyeon (Chem. Comm., 2007, 5167). Alternatively, a method that includes reacting methoxy polyethyleneglycol with phosphoryl chloride ($POCl_3$) to synthesize PO-PEG ligand, ligand exchanging the synthesized PO-PEG ligand with nanoparticles in an organic solvent and dispersing the same in water, has been disclosed. Although this method adopts a relatively simple manufacturing process, phosphoryl chloride ($POCl_3$) readily contacts oxygen to be oxidized in the preparation of ligands, thus causing difficulties in processing such as a requirement for synthesis in an inert atmosphere such as argon or nitrogen. Furthermore, one to three polyethyleneglycols are bonded to a phosphoryl group in the preparation of ligands, thus having a problem in preparing reproducible ligands.

DISCLOSURE

Technical Problem

Therefore, as a result of intensive and extensive efforts to overcome the above problems in the related art, the present inventors have found a dispersion stabilizer capable of modifying the surface of nanoparticles into a hydrophilic state to enable dispersion of the nanoparticles in an aqueous system, and have discovered that a composition of hydrophilic nanoparticles including the foregoing dispersion stabilizer adhered thereto may be effectively used in biomedical applications.

Accordingly, an object of the present invention is to provide a composition of hydrophilic nanoparticles containing a monosaccharide-phosphate or a monosaccharide-phosphate derivative adhered to the surface of the nanoparticles.

Another object of the present invention is to provide a monosaccharide-phosphate derivative formed by combining a monosaccharide-phosphate with a polyethyleneglycol polymer or alcohol having an amine group bonded thereto and, in addition, a composition of hydrophilic nanoparticles containing the above derivative adhered to the surface thereof.

Another object of the present invention is to provide a colloidal solution prepared by dispersing the above composition in water, wherein the composition includes hydrophilic nanoparticles containing a monosaccharide-phosphate or a monosaccharide-phosphate derivative adhered to the surface of the nanoparticles, a contrast agent including the above colloidal solution and, in addition, an imaging method including in vivo injection of the contrast agent.

A still further object of the present invention is to provide a process for modifying the surface of lipophilic nanoparticles with hydrophilic nanoparticles, by contacting a solution, which includes a monosaccharide-phosphate or a monosaccharide-phosphate derivative dispersed in water, with the lipophilic nanoparticles in a polar organic solvent.

Technical Solution

In order to accomplish the above objects, according to one general aspect of the present invention, a composition including nanoparticles that are surface-modified, in turn being dispersed and stabilized, using a monosaccharide-phosphate or its derivative to enable inorganic nanoparticles to be biocompatible and have excellent water-dispersibility, colloidal solution including the same, and a contrast agent including the colloidal solution.

Hereinafter, the present invention will be described in more detail.

The monosaccharide-phosphate used herein may have a structure represented by formula 1:

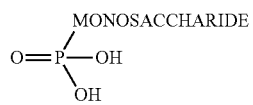

[Formula 1]

In Formula 1, a phosphate group is bonded with one monosaccharide and such monosaccharide used in the present invention may include a monosaccharide having two to nine carbon atoms. Practical examples thereof may include dihydroxy acetone, glyceraldehydes, erythrulose, erythrose, threose, ribulose, xylulose, ribose, arabinose, xylose, lyxose, deoxyribose, pricose, fructose, sorbose, tagatose, allose, altrose, glucose, mannose, gulose, idose, galactose, talose, fucose, fuculose, rhamnose, sedoheptulose, neuraminic acid, etc., without being particularly limited thereto.

According to the present invention, a monosaccharide-phosphate is preferably glucose 6-phosphate, fructose 6-phosphate or mannose 6-phosphate.

According to the present invention, the monosaccharide-phosphate derivative has a structure represented by Formula 2:

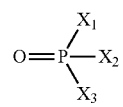

[Formula 2]

In Formula 2,
$X_1$ is a monosaccharide,
$X_2$ is OH, aminoalcohol or polyethyleneglycol, and $X_3$ is OH.

Aminoalcohol is preferably one or two or more selected from ethanolamine, heptaminol, isoetharine, norepinephrine, propanolamine and sphingosine.

Polyethyleneglycol may have amine group at one end or both ends thereof and a molecular weight of 300 to 5,000.

According to the present invention, the nanoparticle may be one or two or more selected from a group consisting of metal, metal chalcogenide, metal oxide, magnetic materials, magnetic alloys, semiconductor materials and multi-component hybrid structures.

According to the present invention, metal may be selected from a group consisting of Pd, Pt, Au, Cu and Ag, metal calcogenide may be selected from $M_xE_y$ (M=Ti, V, Cr, Mn, Fe, Co, Ni, Cu, Zr, Mo, Ru, Rh, Ag, W, Re, Ta, Hf and Zn; E=O, S or Se; 0<x≤3; 0<y≤5), metal oxide may be selected from titanium oxide, vanadium oxide, chromium oxide, manganese oxide, iron oxide, cobalt oxide, nickel oxide, copper oxide, zirconium oxide, molybdenum oxide, ruthenium oxide, rhodium oxide, silver oxide, tungsten oxide, rhenium oxide, tantalum oxide, hafnium oxide and zinc oxide. More preferably, metal oxide is selected from FeO, $Fe_3O_4$ (magnetite), $\alpha$-$Fe_2O_3$, $\beta$-$Fe_2O_3$, $\gamma$-$Fe_2O_3$ (maghemite), $\epsilon$-$Fe_2O_3$, $Fe(OH)_2$, $Fe(OH)_3$, $\alpha$-FeOOH, $\beta$-FeOOH, $\gamma$-FeOOH, $\delta$-FeOOH, $Fe_5HO_8 \cdot 4H_2O$, $5Fe_2O_3 \cdot 9H_2O$, $FeOOH \cdot 4H_2O$, $Fe_8O_8(OH)_6(SO) \cdot nH_2O$, $Fe^{3+}_{16}O_{16}(OH.SO_4)_{12-13} \cdot 10-12H_2O$ and a mixture of $Fe_3O_4$ (magnetite) and $\gamma$-$Fe_2O_2$ (maghemite). Preferably, the magnetic material is selected from a group consisting of Co, Mn, Fe, Ni, Gd, $MM'_2O_4$, $M_xO_y$, (M or M'=Co, Fe, Ni, Mn, Zn, Gd, Cr; 0<x≤3; 0<y≤5), while the magnetic alloys may be selected from a group consisting of CoCu, CoPt, FePt, CoSm, NiFe and NiFeCo. The semiconductor materials may be selected from a group consisting of: semiconductor comprising of elements selected from Groups 2 and 6, respectively; semiconductor comprising of elements selected from Groups 3 and 5, respectively; semiconductor comprising of Group 4 element; semiconductor comprising of elements selected from Groups 4 and 6, respectively; and semiconductor comprising of elements selected from Groups 5 and 6, respectively. The multi-component hybrid structure may include at least two components selected from a group consisting of metal, metal chalcogenide, magnetic materials, magnetic alloys and semiconductor materials and, in addition, a material having a core-shell or heterojunction structure.

The surface-modified hydrophilic nanoparticle may have a size of 1 nm to 200 nm.

The present invention also provides a colloidal solution prepared by dispersing a composition in water, wherein the composition includes hydrophilic nanoparticles having a monosaccharide-phosphate or a monosaccharide-phosphate derivative adhered to the surface of the nanoparticles, a contrast agent including the above colloidal solution and, in addition, an imaging method including in vivo injection of the contrast agent.

The present invention also provides a composition that includes iron oxide nanoparticles having a monosaccharide-phosphate or a monosaccharide-phosphate derivative adhered to the surface of the nanoparticles. The monosaccharide-phosphate is preferably selected from glucose 6-phosphate, fructose 6-phosphate and mannose 6-phosphate. The monosaccharide-phosphate derivative may comprise a monosaccharide-phosphate, of which a phosphate group is bonded with aminoalcohol or polyethyleneglycol and, more preferably, with a specific polyethyleneglycol having amine groups at one end or both ends thereof and a molecular weight of 300 to 50,000. Iron oxide may include a variety of iron oxides and, among them, preferably includes magnetite ($Fe_3O_4$), maghemite ($\gamma$-$Fe_2O_3$) or a mixture thereof. The present invention may provide a colloidal solution prepared by dispersing a composition, which includes iron oxide nanoparticles having a monosaccharide-phosphate or a monosaccharide-phosphate derivative adhered to the surface of the nanoparticles, in water. By adding any of injectable additives, for example, a sodium chloride solution, a solvent such as a dextrose injection, a pH controlling buffer, an isotonic agent to control osmotic pressure to match with blood pressure, an analgesic agent such as glucose, or the like, to the above colloidal solution, to prepare a contrast agent injectable in vivo and, in addition, an imaging method including in vivo injection of the contrast agent.

Further, the present invention may provide colloids prepared by dispersing a composition, which includes hydrophilic iron oxide having a monosaccharide-phosphate or a monosaccharide-phosphate derivative adhered to the surface of the iron oxide, in water, wherein: (i) the iron oxide is magnetite ($Fe_3O_4$), maghemite ($\gamma$-$Fe_2O_3$) or a mixture thereof; and (ii) a difference between a number mean hydrodynamic diameter of a hydrophilic composition and a core diameter of an iron oxide core particle is 6 nm or less, as well as a magnetic resonance imaging (MRI) contrast agent including the above colloids.

In addition, the present invention may provide colloids prepared by dispersing a composition, which includes hydrophilic iron oxide having a monosaccharide-phosphate or a monosaccharide-phosphate derivative adhered to the surface of the iron oxide, in water, wherein: (i) the monosaccharide-phosphate or monosaccharide-phosphate derivative is glucose 6-phosphate or the same having ethanolamine or polyethyleneglycol bonded thereto; (ii) a size of an iron oxide core ranges from 2 nm to 8 nm; and (iii) a number mean hydrodynamic diameter (measured by a dynamic light scattering (DLS) method) of a hydrophilic composition ranges from 2 nm to 15 nm, as well as MRI T1 contrast agent including the above colloids.

Moreover, the present invention may provide colloids prepared by dispersing a composition, which includes hydrophilic iron oxide having a monosaccharide-phosphate derivative adhered to the surface of the iron oxide, in water, wherein: (i) the monosaccharide-phosphate derivative is glucose 6-phosphate having ethanolamine or polyethyleneglycol bonded thereto; (ii) a size of an iron oxide core ranges from 7 nm to 25 nm; and (iii) a number mean hydrodynamic diameter of a hydrophilic composition (measured by a dynamic light scattering (DLS) method) ranges from 7 nm to 50 nm, as well as MRI T2 contrast agent including the above colloids.

Still further, the present invention provides a surface modification process for modifying the surface of nanoparticles into a hydrophilic state by contacting a solution, which includes a monosaccharide-phosphate or a monosaccharide-phosphate derivative dispersed in water, with a lipophilic nanoparticle solution and a polar organic solvent. Here, the core of the lipophilic nanoparticle may be metal, metal chalcogenide, metal oxide, a magnetic material, a magnetic alloy, a semiconductor material or a multi-component hybrid structure and, preferably, iron oxide. The polar organic solvent may be tetrahydrofuran, iso-propanol, n-propanol, methanol, ethanol, dioxane, dimethyl sulfoxide, dimethylformamide, acetonitrile, acetone, acetic acid.

Advantageous Effects

According to the present invention, the surface of inorganic nanoparticles may be modified into a hydrophilic state using a monosaccharide-phosphate or a monosaccharide-phosphate derivative, thereby easily producing a composition of nanoparticles, which are biocompatible and have excellent water-dispersibility, as well as colloids thereof. Such prepared nanoparticle composition may be effectively used in a variety of applications including, for example: in vivo imaging applications such as an MRI contrast agent, computer tomography (CT) contrast agent, etc.; nano-electronic convergence technologies such as a quantum dot light emitting device; biomedical applications such as hyperthermia, or the like. Moreover, compared to a nanoparticle composition dispersed by a dispersion stabilizer known in the art, excellent dispersion stability and a relatively small hydrodynamic diameter may be attained.

MODE FOR INVENTION

Figure 1:
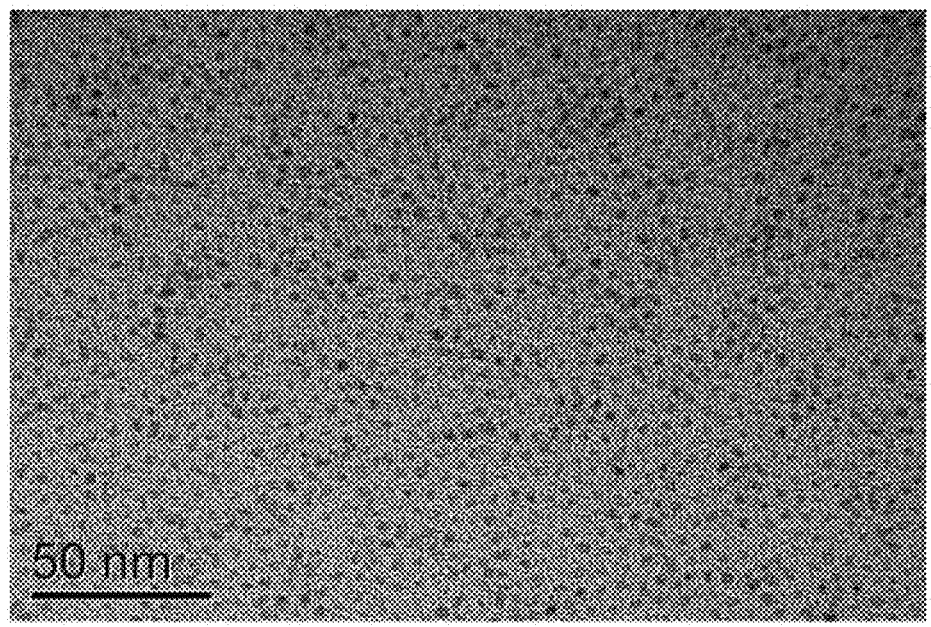
FIG. 1 is a transmission electron microscopy (TEM) image showing iron oxide nanoparticles having oleic acid adhered to the surface with a size of 3 nm, which are dispersed in n-Hexane solvent.
Figure 2:
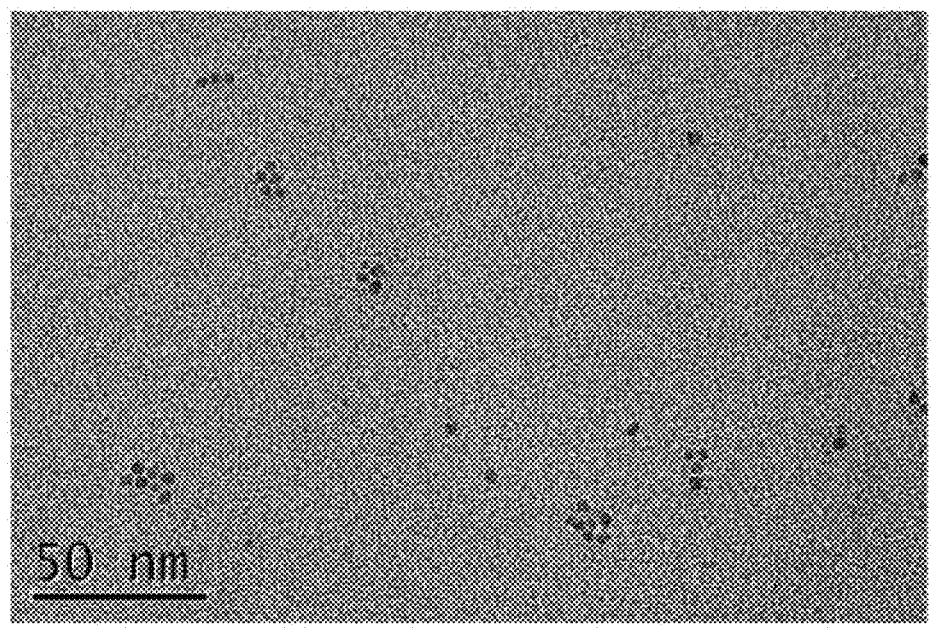
FIG. 2 is a TEM image showing iron oxide nanoparticles with a size of 3 nm dispersed in water according to a method in Example 1.
Figure 3:
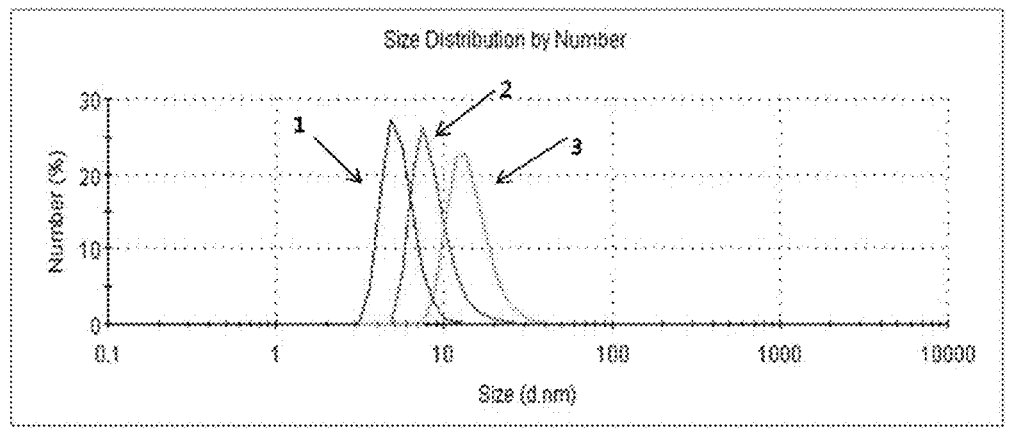
FIG. 3 illustrates measured results of the hydrodynamic diameter of iron oxide nanoparticles dispersed in water according to methods in Examples 1, 2 and 3, wherein (1) shows nanoparticles obtained by hydrophilization of iron oxide nanoparticles having a size of 3 nm with glucose 6-phosphate, thus having a hydrodynamic diameter of 3.8 nm; (2) shows nanoparticles obtained by hydrophilization of iron oxide nanoparticles having a size of 7 nm with mannose 6-phosphate, thus having a hydrodynamic diameter of 8.7 nm; and (3) shows nanoparticles obtained by hydrophilization of iron oxide nanoparticles having a size of 10 nm with fructose 6-phosphate, thus having a hydrodynamic diameter of 11.3 nm.

The advantages, features and aspects of the present invention will become apparent from the following description of the embodiments with reference to the accompanying drawings, which is set forth hereinafter. The technical spirit of the present invention may be easily embodied by those having ordinary knowledge in the art to which the present invention pertains. In addition, technical and/or scientific terminologies used in the detailed description herein have meanings generally understood by those skilled in the related art, to which the present invention pertains, unless otherwise stated. In the following description and the accompanying drawings, a detailed description of technical configurations and/or functions well known in the art will be omitted for brevity without undesirably making the essentials of the present invention unclear.

The present invention provides a composition of nanoparticles having a monosaccharide-phosphate or a monosaccharide-phosphate derivative adhered to the surface thereof.

The monosaccharide-phosphate used herein may be in any form of glucose 6-phosphate, fructose 6-phosphate or mannose 6-phosphate, and may be dispersed in water. The monosaccharide-phosphate derivative used herein may be monosaccharide-phosphate-polyethyleneglycol comprising glucose 6-phosphate, fructose 6-phosphate or mannose 6-phosphate, of which a phosphate group is bonded with a polyethyleneglycol-based biocompatible polymer affinitive to an aqueous medium, and/or monosaccharide-phosphate-aminoalcohol combined with alcohol having an amine group bonded thereto.

A structure of a monosaccharide-phosphate may be represented by Formula 1:

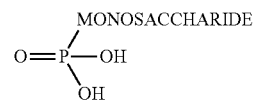

[Formula 1]

In Formula 1, a phosphate group is bonded with one monosaccharide and such monosaccharide used in the present invention may include a monosaccharide having two to nine carbon atoms. Practical examples thereof may include dihydroxy acetone, glyceraldehydes, erythrulose, erythrose, threose, ribulose, xylulose, ribose, arabinose, xylose, lyxose, deoxyribose, pricose, fructose, sorbose, tagatose, allose, altrose, glucose, mannose, gulose, idose, galactose, talose, fucose, fuculose, rhamnose, sedoheptulose, neuraminic acid, etc., without being particularly limited thereto.

Alternatively, a polysaccharide may be bonded at a site of a monosaccharide and such polysaccharide may include disaccharides, trisaccharides, tetrasaccharides, oligosaccharides and polysaccharides. Practical examples thereof may include sucrose, lactose, maltose, trehalose, turanose, cellobiose, raffinose, melecitose, maltotriose, acarbose, starch, fructo-oligosaccharide, galacto-oligosaccharide, mannan-oligosaccharide, clucan, glycogen, amylose, amylopectin, cellulose, dextrane, maltodextrin, tructane, mannan, galactane, etc., without being particularly limited thereto.

A structure of monosaccharide phosphate derivative may be represented by Formula 2:

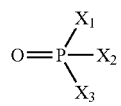

[Formula 2]

In Formula 2, $X_1$ is monosaccharide, preferably, glucose, fructose or mannose.

$X_2$ is OH, aminoalcohol or polyethyleneglycol.

For aminoalcohol, for example, ethanolamine, heptaminol, isoetharine, norepinephrine, propanolamine and sphingosine.

Polyethyleneglycol may be $(OCH_2CH_2)_nOH$, $(OCH(CH_2)CO)_nOH$ or $(OCH_2CO)_nOH$, and n is an integer ranging from 1 to 1200. Preferably, polyethyleneglycol has amine groups at one end or both ends and a molecular weight of 300 to 50,000. Combination of the derivative to monosaccharide-phosphate may include any reaction to form a covalent bond between two molecules.

Combination of aminoalcohol may be accomplished using 1-ethyl-3-[3-dimethylaminopropyl]carbodiimide (EDC) and N-hydroxy succinimide (NHS), to form a phosphoramidate bond between a phosphate group and an amine group of aminoalcohol. Combination of polyethyleneglycol may be achieved by covalent bonding ethylene diamine $(C_2H_8N_2)$ with a phosphate group through EDC and NHS to prepare a monosaccharide-phosphate ethylenediamine, and then, covalent bonding the prepared one with the polyethyleneglycol having a carboxyl group at one end thereof through EDC and NHS or, otherwise, using EDC and NHS to form a covalent bond between PEG having an amine group at one end thereof and a monosaccharide-phosphate.

$X_3$ is OH.

Among monosaccharide-phosphates, glucose 6-phosphate is a material generated during glycolysis and enriched in vivo, thus being biocompatible. Alternatively, other monosaccharide-phosphates and monosaccharide-phosphate derivatives may also be expected to have excellent biocompatibility.

Nanoparticles may be selected from metal, metal chalcogenide, metal oxide, magnetic materials, magnetic alloys, semiconductor materials and/or multi-component hybrid structures. A nanoparticle may have a lipophilic ligand bonded to the surface thereof. For instance, for iron oxide, nanoparticles synthesized by thermal decomposition may contain an organic material due to oleic acid, an organic material due to a synthesis solvent or an organic material due to a precipitate adhered to the surface of the nanoparticles. The organic material adhered to the surface of the nanoparticles may be mostly removed by a method according to the present invention, thereby resulting in a nanoparticle composition having hydrophilic properties. A diameter of the nanoparticle may range from 1 nm to 200 nm, preferably, 1 nm to 50 nm.

Metal nanoparticles may be selected from a group consisting of Pd, Pt, Au, Cu and Ag; metal chalcogenide may be selected from $M_xE_y$ (M=Ti, V, Cr, Mn, Fe, Co, Ni, Cu, Zr, Mo, Ru, Rh, Ag, W, Re, Ta, Hf and Zn; E=O, S or Se; $0<x\leq3$; $0<y\leq5$); and metal oxide may be selected from titanium oxide, vanadium oxide, chromium oxide, manganese oxide, iron oxide, cobalt oxide, nickel oxide, copper oxide, zirconium oxide, molybdenum oxide, ruthenium oxide, rhodium oxide, silver oxide, tungsten oxide, rhenium oxide, tantalum oxide, hafnium oxide and zinc oxide. Among metal oxides, practical examples of iron oxide may be selected from FeO, $Fe_3O_4$ (magnetite), $\alpha$-$Fe_2O_3$, $\beta$-$Fe_2O_3$, $\gamma$-$Fe_2O_3$ (maghemite), $\epsilon$-$Fe_2O_3$, $Fe(OH)_2$, $Fe(OH)_3$, $\alpha$-FeOOH, $\beta$-FeOOH, $\gamma$-FeOOH, $\delta$-FeOOH, $Fe_5HO_8 \cdot 4H_2O$, $5Fe_2O_3 \cdot 9H_2O$, $FeOOH \cdot 4H_2O$, $Fe_8O_8(OH)_6(SO) \cdot nH_2O$, $Fe^{3+}_{16}O_{16}(OH \cdot SO_4)_{12-13} \cdot 10-12H_2O$ or a mixture of $Fe_2O_4$ (magnetite) and $\gamma$-$Fe_2O_3$ (maghemite). On the other hand, the magnetic material may be selected from a group consisting of Co, Mn, Fe, Ni, Gd, $MM'_2O_4$, $M_xO_y$ (M or M'=Co, Fe, Ni, Mn, Zn, Gd, Cr; $0<x\leq3$; $0<y\leq5$), while the magnetic alloys may be selected from a group consisting of CoCu, CoPt, FePt, CoSm, NiFe and NiFeCo. The semiconductor materials may be selected from a group consisting of: semiconductor comprising of elements selected from Groups 2 and 6, respectively; semiconductor comprising of elements selected from Groups 3 and 5, respectively; semiconductor comprising of Group 4 element; semiconductor comprising of elements selected from Groups 4 and 6, respectively; and semiconductor comprising of elements selected from Groups 5 and 6, respectively. The multi-component hybrid structure may include at least two components selected from a group consisting of metal, metal chalcogenide, magnetic materials, magnetic alloys and semiconductor materials and, in addition, a material having a core-shell or heterojunction structure.

A method for preparation of a composition, which includes nanoparticles having a monosaccharide-phosphate or a monosaccharide-phosphate derivative adhered to the surface thereof, may include contacting nanoparticles with a solvent and a solution in which the monosaccharide-phosphate or the monosaccharide-phosphate derivative is dissolved. Such monosaccharide-phosphate or monosaccharide-phosphate derivative may be used as an aqueous solution containing the same dissolved in water. Nanoparticles may be hydrophilic or hydrophobic (that is, lipophilic), therefore, be dispersed in water or an organic solvent. In order to appropriately contact a monosaccharide-phosphate or a monosaccharide-phosphate derivative with nanoparticles and a solvent, a water-affinitive solvent, for example, a polar solvent such as tetrahydrofuran, iso-propanol, n-propanol, methanol, ethanol, dioxane, dimethyl sulfoxide, dimethylformamide, acetonitrile, acetone, acetic acid, etc. may be suitably used. It is considered that the material adhered to the surface of nanoparticles by a monosaccharide-phosphate or a monosaccharide-phosphate derivative undergoes exchange (ligand exchange). A part of the monosaccharide or monosaccharide derivative may surround nanoparticles in a micelle form.

The present invention provides a colloidal solution including a composition dispersed in water, wherein the composition includes iron oxide nanoparticles having a monosaccharide-phosphate or a monosaccharide-phosphate derivative adhered to the surface of the nanoparticles. In order to inject the colloidal solution in vivo, a variety of injectable additives, for example; a sodium chloride solution, a solvent such as a dextrose injection, a pH controlling buffer, an isotonic agent to control osmotic pressure to match with blood pressure, an analgesic agent such as glucose, or the like, may be added thereto, to prepare a contrast agent. Furthermore, an imaging method including in vivo injection of the contrast agent may be provided. Such in vivo injection method may include intravenous injection, oral administration, inhalation, etc., and intravenous injection is most preferably used. The imaging method may include, for example, MRI (magnetic resonance imaging), X-ray, CT, PET, SPECT, etc. and, among them, MRI is most preferably used. Contrast imaging through MRI may include, for example, negative contrast (T2, darkening) and/or positive contrast (T1, brightening). If a size of the used iron oxide and a number mean hydrodynamic diameter of the hydrophilized composition are not more than 5 nm and 15 nm, respectively, positive contrast imaging is preferably used. On the contrary, in the case where the size of the used iron oxide and the number mean hydrodynamic diameter of the hydrophilized composition exceed 5 nm and 15 nm, respectively, negative contrast imaging is more preferable. If it is possible to decrease a thickness of the hydrophilized surface of the iron oxide, a hydrophilized nanoparticle composition having a slightly larger size than a core size of the iron oxide may be obtained. Therefore, the hydrodynamic diameter may be controlled with high precision. In order to improve long term stability of nanoparticles in water, steric hindrance and electrostatic repulsion may be utilized. Surface coating or ligand exchanging with a hydrophilic polymers has been used in the art. But, polymers make the hydrodynamic diameter too thick. When small molecules are attached to the surface of nanoparticle, a hydrodynamic diameter can be reduced. But, long term stability in water is deteriorated and biocompatibility is restricted. Consequently, there is a strong need for enhancing long term stability while decreasing a hydrodynamic diameter of a particle.

The present invention also describes colloids and an MRI contrast agent with long blood retention time including the colloids. The colloids are prepared by dispersing a composition, which includes hydrophilic iron oxide nanoparticle having a monosaccharide-phosphate or a monosaccharide-phosphate derivative adhered to the surface, in water, wherein: (i) the iron oxide is magnetite ($Fe_3O_4$), maghemite ($\gamma$-$Fe_2O_3$) or a mixture thereof; and (ii) a difference between a number mean hydrodynamic diameter of a hydrophilic composition and a core diameter of iron oxide core particle is 6 nm or less. In the case where the difference in size between the hydrodynamic diameter of the hydrophilic composition and the diameter of the iron oxide core is small, the hydrophilized nanoparticle composition may a larger retention time in blood. Existing MRI contrast agents, i.e., Gd-complex (Magnevist-Bayer Schering Co., Omniscan-GE Healthcare Co.) has a very short BHL of several minutes or less, while an iron oxide-based contrast agent (Feridex-AMAG Co., Resovist-Gayer Schering Co.) is delivered into and distributed in the liver within several tens of minutes by macrophage. Accordingly, there is a strong need for a novel and improved hydrophilization method that extends a blood retention time or BHL (blood half life) by decreasing a hydrodynamic diameter of an iron oxide nanoparticle composition after hydrophilization.

Further, the present invention describes colloids and T1 MRI contrast agent including the colloids. The Colloids are prepared by dispersing a composition, which includes hydrophilic iron oxide particle having a monosaccharide-phosphate or a monosaccharide-phosphate derivative adhered to the surface, in water, wherein: (i) the monosaccharide-phosphate or monosaccharide-phosphate derivative is selected from glucose 6-phosphate or its derivative having ethanolamine or polyethyleneglycol bonded thereto; (ii) a size of an iron oxide core ranges from 2 nm to 8 nm; and (iii) a number mean hydrodynamic diameter (measured by a dynamic light scattering (DLS) method) of a hydrophilic composition ranges from 2 nm to 15 nm. If the iron oxide core is small, the ratio of T2 relaxivity (r2) and T1 relaxivity (r1) [r2/r1] is reduced, thereby execution of positive contrast (T1) is enabled. As shown in Example (in vitro MRI test), the hydrophilized iron oxide composition with a small core diameter which are formed by glucose 6-phosphate or glucose 6-phosphate ethanolamine or glucose 6-phosphate polyethyleneglycol show relatively high 'r1' and low 'r2', thus show low r2/r1. A contrast agent containing the above colloids was injected through a tail vein of a rat to execute MRI positive contrast and, as a result, distinct and bright images (positive contrast) were obtained as shown in Examples 7-1, 8-1 and 8-2. Until 1 hour or 2 hours, the blood vessel was brightly contrasted, however after 24 hours, completely lost image brightness for contrasting. From such result, it is presumed that, although the contrast agent resides several hours, it is completely removed from the blood vessel after about 1 day. Accordingly, it can be understood that angiographic imaging is possibly executed using the foregoing contrast agent.

The present invention also describes colloids and a T2 MRI contrast agent including the colloids. The colloids are prepared by dispersing a composition, which includes hydrophilic iron oxide particle having a monosaccharide-phosphate derivative adhered to the surface, in water, wherein: (i) the monosaccharide-phosphate derivative is glucose 6-phosphate ethanolamine or glucose 6-phosphate polyethyleneglycol; (ii) a size of an iron oxide core ranges from 7 nm to 25 nm; and (iii) a number mean hydrodynamic diameter of a hydrophilic composition (measured by a dynamic light scattering (DLS) method) ranges from 7 nm to 50 nm. The iron oxide core is relatively large, and T2 relaxation rate (r2) is sharply increased while T1 relaxation rate (r1) is almost the same. Therefore, r2/r1 is significantly increased, in turn negative contrast effects (T2) is increased.

As a result, negative contrast (T2) is advantageously executed while positive contrast becomes substantially impossible. As shown in Example 10 (in vitro MRI test), the hydrophilized iron oxide composition with a large core diameter which are formed by glucose 6-phosphate ethanolamine or glucose 6-phosphate polyethyleneglycol show relatively low 'r1' and high 'r2', thus show high r2/r1. A contrast agent containing the above colloids was injected through a tail vein of a rat to execute MRI negative contrast and, as a result, strong negative contrast (darkening) was obtained in lymph nodes after 1 day as shown in Examples 8-3 and 9. From such result, it can be understood that using the foregoing contrast agent may enable imaging of biotissues such as lymph nodes with negative contrast (T2).

The colloids including a composition, which includes hydrophilic iron oxide having a monosaccharide-phosphate or a monosaccharide-phosphate derivative adhered to the surface thereof, provided by the present invention, exhibit no or very little toxicity in vivo. As shown in Example 11, the result of cytotoxicity test demonstrated that all nanoparticles, that is, (A) 10 nm iron oxide nanoparticles stabilized by glucose 6-phosphate, (B) 10 nm iron oxide nanoparticles stabilized by glucose 6-phosphate-PEG derivatives, and (C) 3 nm iron oxide nanoparticles stabilized by glucose 6-phosphate-aminoalcohol, do not influence cellular viability up to a concentration of 200 ppm, thereby exhibiting superior biocompatibility.

Hereinafter, exemplary embodiments will be described in detail with reference to the accompanying drawings.

Example 1

Composition Including Iron Oxide Nanoparticles Hydrophilized by Glucose 6-Phosphate Dispersion was prepared by dispersing 100 mg of iron oxide ($Fe_3O_4$) having oleic acid adhered to the surface thereof and a size of 3 nm in 8 ml of tetrahydrofuran (THF). A solution was prepared by dissolving 200 mg of glucose 6-phosphate sodium salt in 2 ml of distilled water (DIW). The dispersion and the solution were mixed. The mixture was agitated and heated at 60° C. for 4 hours, followed by settling and cooling the reaction product. The top THF layer was removed, resulting in a composition including hydrophilic iron oxide. Adding DIW to the composition, a colloidal solution was prepared. The colloidal solution was left at room temperature for six (6) months, a change in turbidity was not observed to demonstrate excellent long term stability.

Hydrodynamic diameter of the nanoparticle composition in the colloidal solution was measured using Malvern Zetasizer Nano ZS. The hydrodynamic diameter was about 3.8 nm, which is substantially similar to the core size (3 nm). After 6 months, the hydrodynamic diameter was 3.9 nm.

Example 2

Preparation of Composition Including Iron Oxide Nanoparticles Hydrophilized by Mannose 6-Phosphate According to the same procedure described in Example 1, 7 nm iron oxide nanoparticles were dispersed in water using mannose 6-phosphate sodium salt. Using Malvern Zetasizer Nano ZS, a hydrodynamic diameter measured to be 8.7 nm, thus demonstrating the size substantially similar to the core size (7 nm).

Example 3

Preparation of Composition Including Iron Oxide Nanoparticles Hydrophilized by Fructose 6-Phosphate According to the same procedure described in Example 1, 10 nm iron oxide nanoparticles were dispersed in water using fructose 6-phosphate sodium salt. Using Malvern Zetasizer Nano ZS, a hydrodynamic diameter was measured to be 11.3 nm, thus demonstrating the size substantially similar to the core size (10 nm).

Example 4

Synthesis of Glucose 6-Phosphate Polyethyleneglycol

Example 4-1

Synthesis of Phosphate-Diethylamine

After dissolving 1 g of glucose 6-phosphate sodium salt in 10 ml of 2-(N-morpholino)ethane sulfonic acid (MES) buffer solution, 0.68 g of 1-ethyl-3-[3-dimethylaminopropyl] carbodiimide hydrochloride (EDC) and 0.4 g of N-hydroxy succinimide (NHS) are mixed with the solution and maintained for 30 minutes. Then, 0.23 ml of diethylamine was added to the mixture, resulting in glucose 6-phosphate-diethylamine.

Example 4-2

Synthesis of Glucose 6-Phosphate-Diethylamine-PEG

After dispersing 17.75 g of methoxy polyethyleneglycol carboxyl (mPEG-COOH, 5000) in 40 ml of MES buffer solution, 1.361 g of EDC and 0.817 g of NHS were added to the dispersion and agitated for 30 minutes. Then, after adding glucose 6-phosphate-diethyl amine synthesized in Example 4-1 to the above solution, the mixture was agitated for 1 day. Following this, unreacted material and a byproduct were removed through dialysis, followed by removal of water.

Example 5

Synthesis of Glucose 6-Phosphate Ethanolamine

After dissolving 1 g of glucose 6-phosphate sodium salt in 10 ml of MES buffer solution, 0.68 g of EDC and 0.4 g of NHS were mixed with the solution and maintained for 30 minutes. Then, 0.22 ml of ethanolamine (2-aminoethanol) was added to the mixture, resulting in glucose 6-phosphate aminoalcohol.

Example 6

Preparation of Composition of Iron Oxide Nanoparticles that Include Glucose 6-Phosphate Ethanolamine Adhered to the Surface Using the glucose 6-phosphate derivatives in Example 4 and 5, nanoparticle compositions were prepared by the same procedure according to Example 1.

Example 7

In Vivo Magnetic Resonance Imaging Experiment with Colloidal Solution of Iron Oxide Nanoparticles Hydrophilized by Monosaccharide Phosphate According to the methods proposed in Examples 1, 2 and 3, a composition including iron oxide nanoparticles hydrophilized in water and its colloidal solution were prepared, followed by analysis of a hydrodynamic diameter using a Malvern Zeta sizer Nano ZS device.

For the colloidal solution of iron oxide nanoparticles surface-modified using monosaccharide phosphate and the colloidal solution of iron oxide nanoparticles hydrophilized by the methods described in Comparative Examples 1 and 2, hydrodynamic diameters are listed in Table 1. For the iron oxide nanoparticle surface-modified using monosaccharide phosphate, it was found that a difference between a core size and a number mean hydrodynamic diameter were much smaller, compared to Comparative Examples 1 and 2.

TABLE 1

| Iron oxide core size | Material for hydro-philization | Hydro-dynamic diameter (volume mean) (nm) | Hydro-dynamic diameter (number mean) (nm) | Difference between number mean hydrodynamic diameter and core size (nm) |
|---|---|---|---|---|
| 2 nm | PO-Glu | 4.0 | 3.2 | 1.2 |
| 3 nm | PO-Glu | 6.7 | 3.8 | 0.8 |
| 4 nm | PO-Glu | 6.0 | 4.7 | 0.7 |
| 7 nm | PO-Glu | 9.7 | 8.0 | 1.0 |
| 10 nm | PO-Glu | 23.4 | 15.3 | 5.3 |
| 20 nm | PO-Glu | 38.6 | 23.0 | 3.0 |
| 2 nm | PO-Man | 8.9 | 7.9 | 5.9 |
| 7 nm | PO-Man | 14.4 | 8.7 | 1.7 |
| 10 nm | PO-Man | 20.6 | 14.1 | 4.1 |
| 2 nm | PO-Fru | 6.0 | 5.2 | 3.2 |
| 7 nm | PO-Fru | 18.5 | 12.5 | 5.5 |
| 10 nm | PO-Fru | 23.6 | 11.3 | 1.3 |
| 10 nm (Comparative Example 1) | PLGA | 46 | 42 | 32 |
| 3 nm (Comparative Example 2) | PO-PEGs | 21 | 15 | 12 |

*PO-Glu: Glucose 6-phosphate, PO-Man: Mannose 6-phosphate, PO-Fru: Fructose-6-phosphate

Example 7-1

Magnetic Resonance T1 Imaging Experiment with Composition Including Glucose 6-Phosphate-Bonded 3 nm Core Iron Oxide Nanoparticles Using a wrist coil in MRI scanner (Trio 3.0T, Siemens), the colloidal solution containing iron oxide nanoparticles dispersed and hydrophilized therein was subjected to evaluation of in vivo T1 imaging performance, as shown in Table 1.

The evaluation of in vivo T1 imaging performance was executed with rat F-344. The rat weighed 200 to 300 g. After anesthetizing, the rat was placed horizontally in the MRI scanner and cross-sections thereof were observed. MRI images of the rat were taken before, immediately after, 2 hours after and 24 hours after injection of a contrast agent, respectively, in order to observe and compare blood vessels of the rat before and after the injection of the contrast agent. Adding 5% glucose solution (Joong-wea (JW) Pharmaceutical) to the colloidal solution of 3 nm core iron oxide nanoparticles shown in Table 1, the contrast agent was prepared. Iron content was analyzed through ICP-AES and an administration dose was calculated in consideration of the weight of mouse, to prepare a contrast agent with a total volume of 1 ml. The contrast agent was injected through a tail vein of the rat in an amount of 5.2 mg Fe/kg (rat).

Determination of in vivo T1 relaxation performance was executed using 3D SPGR sequence (TR/TE: 25/5.1, Flip angle: 25°), a scan time was 12 minutes, an image thickness was 1 mm, the number of lattices was 256×146 and FOV was 65×110 mm.

In order to quantify T1 contrast imaging effects of the prepared contrast agent, one was selected among cross-sections of the highest visible parts, that is, the aorta, subclavian vein, right atrium and axillary vein, and a bright part thereof was selected as ROI (Region of Interest) in order to measure signal intensity thereof. Since an overall signal intensity of the acquired MRI images is altered whenever it is measured, relative signal intensity (SNR: Signal to Noise Ratio) was determined using saline as a noise. Comparing SNR before and after using the contrast agent, T1 signal enhancement ratio (ΔR1) was calculated and results thereof are illustrated by the graphs in the figure. The following Equation 1 is a method for calculation of T1 signal enhancement ratio (ΔR1).

$$T1\ \text{signal enhancement ratio}(\Delta R1) = 100 \times [1 - (SNR_t/SNR_0)] \quad [\text{Equation 1}]$$

$SNR_0$ (SNR before administration of contrast agent) = [Signal intensity of $ROI_0$/Signal intensity of $muscle_0$]

$SNR_t$ (SNR after administration of contrast agent) = [Signal intensity of $ROI_t$/Signal intensity of $muscle_t$]

Figure 4:
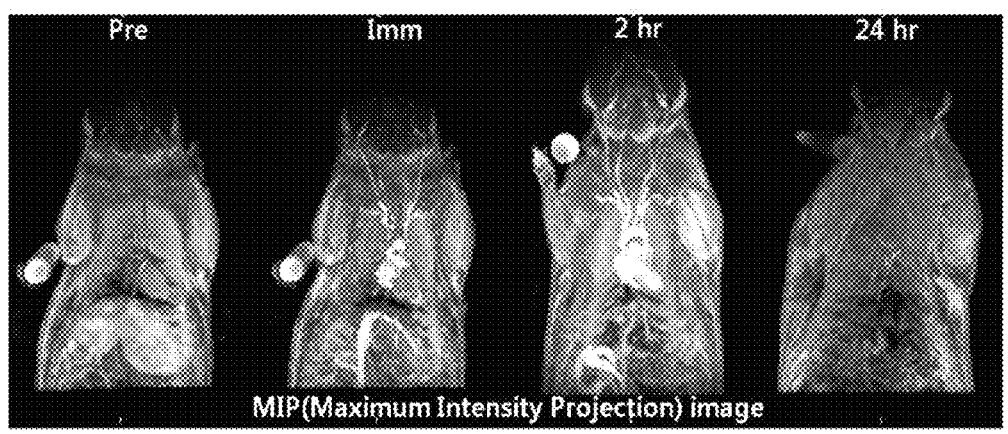
FIG. 4 is in vivo angiographic image of a rat in Example 7-1.

FIG. 4 is an MRI T1 angiographic image of a rat taken by injecting a contrast agent into a rat, wherein the contrast agent includes colloids formed by dispersing a composition, which includes core iron oxide nanoparticles having a size of 3 nm hydrophilized therein, in water. It can be confirmed the blood vessels of the rat is observed as white highlighted part (positive contrast) and the contrast agent resides in vivo for 2 hours or more. For existing gadolinium contrast agent, since in vivo retention time is very short such as less than 1 minute, MRI scan time for imaging cannot be extended, thus not acquiring high resolution images. In contrast, the iron oxide contrast agent prepared according to the present invention has a relatively long in vivo retention time, thus enabling imaging while elongating the scan time. Therefore, it is confirmed that high resolution images may be obtained and even micro-vascular parts can be observed.

Figure 5:
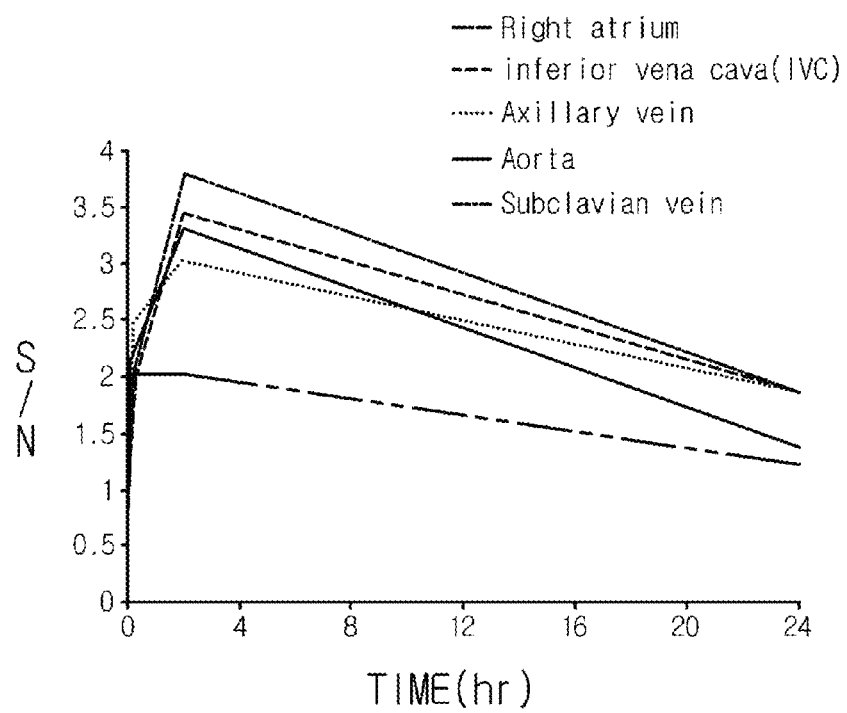
FIG. 5 illustrates a signal intensity of in vivo angiographic image of the rat in Example 7-1 in a signal to noise ratio.

FIG. 5 illustrates MR signal intensities and demonstrates that brightness is increased by 4 times at the maximum, compared to before injection of the contrast agent. Moreover, it was confirmed that even the subclavian vein having a size of 0.2 mm can be clearly observed.

Example 8

In Vivo MRI Image Formation with Contrast Agent Hydrophilized Using Glucose 6-Phosphate Ethanolamine According to the method proposed in Example 7, iron oxide nanoparticles hydrophilized using glucose 6-phosphate ethanolamine were prepared.

For colloidal solutions of iron oxide nanoparticles surface-modified using a glucose 6-phosphate ethanolamine, hydrodynamic diameters are listed in Table 2.

TABLE 2

| Core size | Vol. mean (nm) | No. mean (nm) |
|---|---|---|
| 3 nm | 18 | 8 |
| 10 nm | 14 | 9 |

Example 8-1

Figure 6:
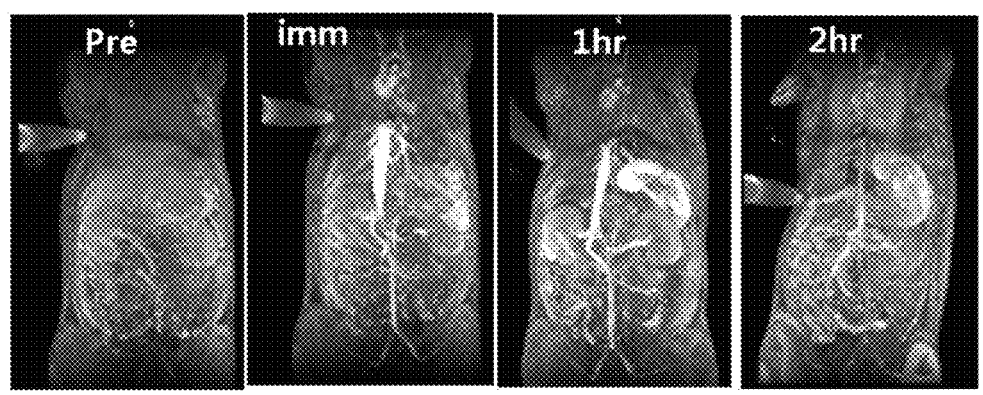
FIG. 6 is in vivo angiographic image of a rat in Example 8-1.

Rat Angiographic T1 Contrast Agent of Composition Including 3 nm Iron Oxide Hydrophilized Using Glucose 6-Phosphate Ethanolamine Iron oxide nanoparticles having a core size of 3 nm hydrophilized using glucose 6-phosphate ethanolamine were used for T1 angiographic contrast imaging by the same method described in Example 7-1. Results thereof are shown in FIG. 6.

Figure 7:
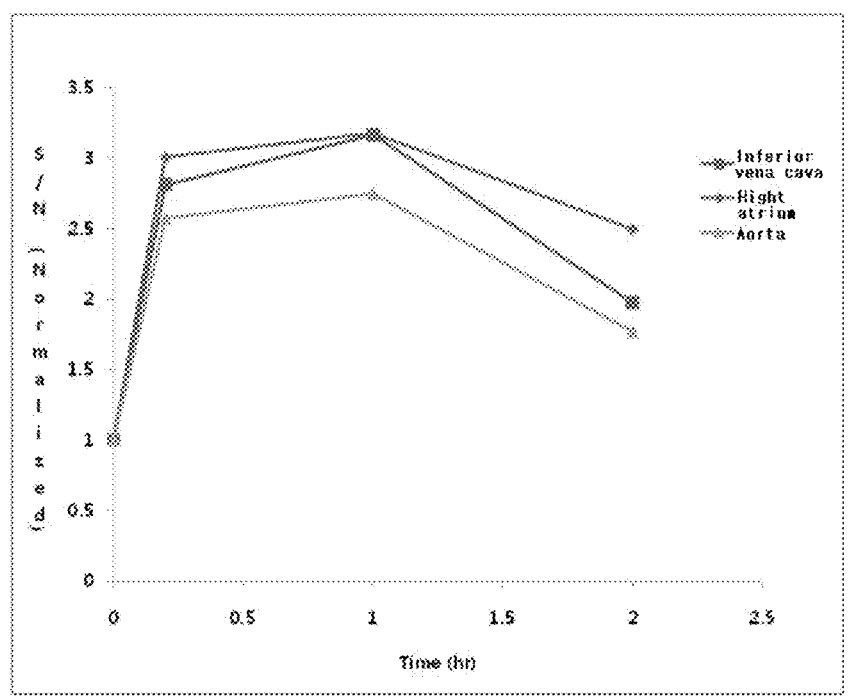
FIG. 7 illustrates a signal intensity of in vivo angiographic image of the rat in Example 8-1 in a signal to noise ratio, specifically, signal intensities of the right atrium, the inferior vena cava (IVC), the aorta, etc.

After treating the above results according to Equation 1 in Example 7-1, results thereof are shown in FIG. 7. From the figure, it can be seen that signals in the inferior vena cava, right atrium and aorta are noticeably increased.

Example 8-2

Figure 8:
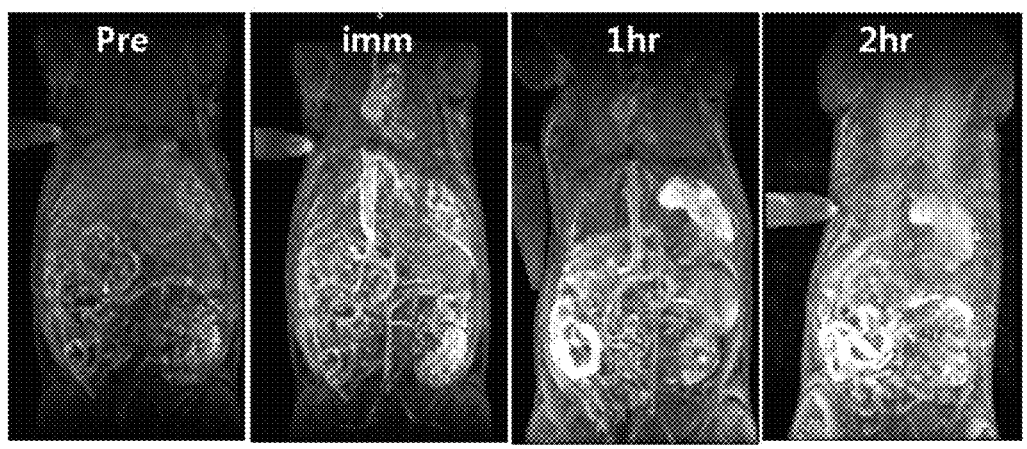
FIG. 8 is in vivo angiographic image of a rat in Example 8-2.

Rat Angiographic T1 Contrast Imaging with 7 nm Iron Oxide Hydrophilized Using Glucose 6-Phosphate Ethanolamine Iron oxide nanoparticles having a core size of 7 nm hydrophilized using glucose 6-phosphate ethanolamine were used for T1 angiographic contrast imaging by the same method described in Example 8. Results thereof are shown in FIG. 8.

Figure 9:
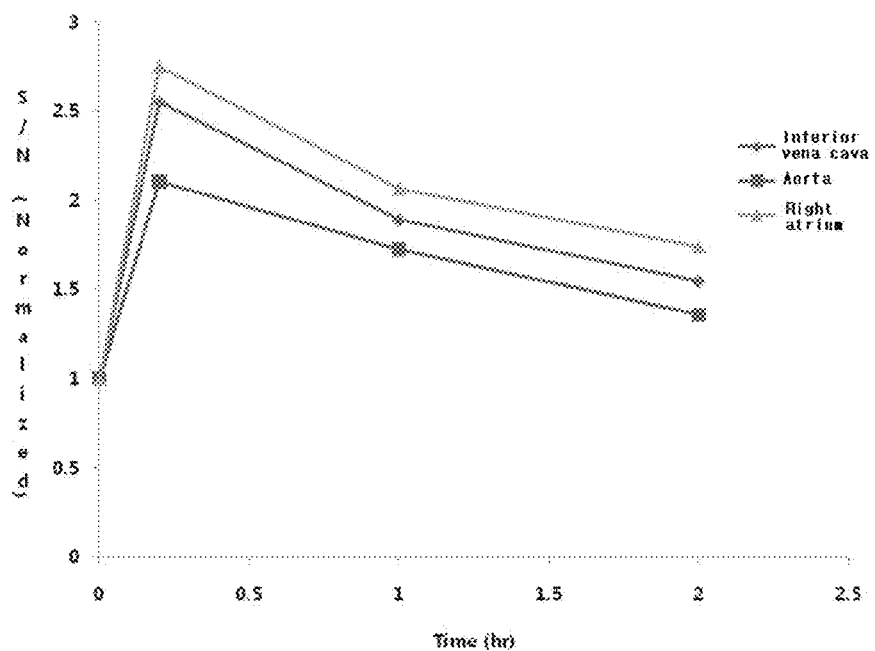
FIG. 9 illustrates a signal intensity of in vivo angiographic image of the rat in Example 8-2 in a signal to noise ratio, specifically, signal intensities of the right atrium, the inferior vena cava (IVC), the aorta, etc.

After treating the above results according to Equation 1 in Example 7-1, results thereof are shown in FIG. 9. From the figure, it can be seen that signals in the inferior vena cava, right atrium and aorta are noticeably increased.

Example 8-3

T2 Contrast Imaging of Mouse Lymph Node with Composition Including 7 nm Iron Oxide Hydrophilized Using Glucose 6-Phosphate Ethanolamine In order to evaluate applicability of iron oxide nanoparticles having a core size of 7 nm hydrophilized using glucose 6-phosphate aminoalcohol as an MRI contrast agent, in vivo T2 relaxation performance was measured using a loop coil in an MRI scanner (Trio 3.0T, Siemens).

Evaluation of in vivo relaxation performance was executed with a nude mouse (BALB/c nude mouse) and the mouse weighed about 20 to 30 g. After anesthetizing, the mouse was placed horizontally in the MRI scanner, followed by observing cross-section thereof. The MRI images of the nude mouse were subjected to measurement before and 24 hours after injecting the contrast agent, and lymph nodes before and after injection of the contrast agent were observed and compared to each other. The contrast agent was dispersed in 0.5 ml of 5% DW and iron content was measured through ICP-AES. Also, the contrast agent was injected through a tail vein of the mouse with an administration dose of 10.4 mg Fe/kg in consideration of the weight of mouse.

Determination of in vivo T2 relaxation performance was conducted using T2Me3d pulse sequences provided by Siemens Co., and particular parameters are as follows.

TR (repetition time)=40.0 msec, TE (echo time)=22.0 msec, FOV=49 mm×70 mm, Matrix size=256×180, slice thickness=0.6 mm, number of acquisition=6

In order to quantify T2 attenuation effects of the prepared contrast agent, each cross-section was selected from the highest visible lymph nodes, that is, inguinal lymph node and brachial lymph node and discolored parts thereof were selected as ROI (Region of Interest) in order to measure signal intensity thereof. Since an overall signal intensity of the acquired MRI images is altered whenever it is measured, absolute value of the signal intensity (S) is not proper to evaluate contrast imaging performance. Therefore, for the inguinal lymph node, the right hind leg muscle was used as a control (N: noise). On the other hand, for the brachial lymph node, the right paw muscle was used as a control (N: noise). Compared to the controls, relative signal intensity (SNR: Signal to Noise Ratio) was calculated. By comparing SNR values before and after using the contrast agent, T2 signal attenuation ratio ($\Delta R2$) was calculated. The results are illustrated by the graphs in FIG. 11. The following Equation 2 is a method for calculation of T2 signal attenuation ratio ($\Delta R2$).

$$T2 \text{ signal attenuation ratio}(\Delta R2)=100\times[1-(SNR_t/SNR_0)] \quad \text{[Equation 2]}$$

$SNR_0$(SNR before administration of contrast agent)=
[Signal intensity of $ROI_0$/Signal intensity of $muscle_0$]

$SNR_t$(SNR after administration of contrast agent)=
[Signal intensity of $ROI_t$/Signal intensity of $muscle_t$]

Figure 10:
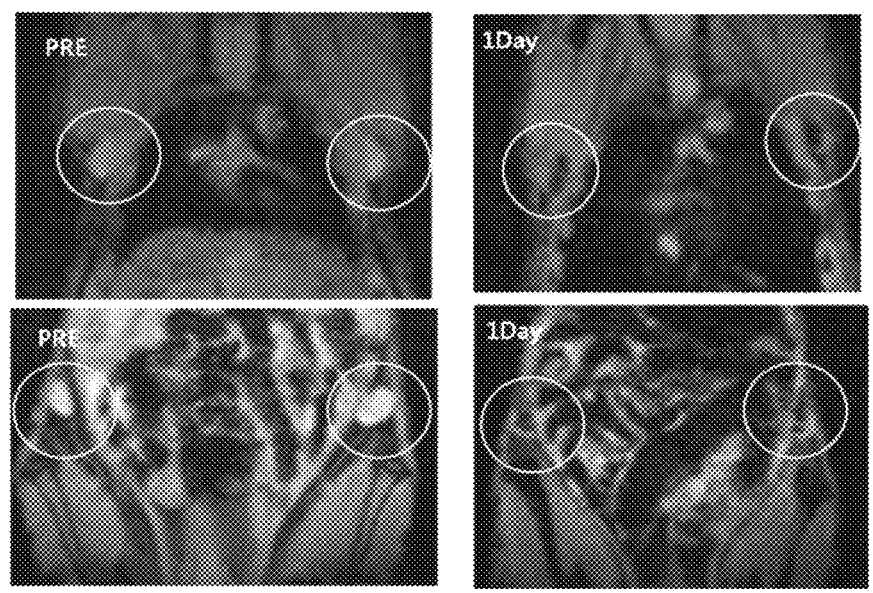
FIG. 10 is in vivo MRI lymph node contrast image of a mouse in Example 8-3, wherein images before injection (PRE) and 1 day after injection (1 Day) are included, and the image at the top end indicates a brachial lymph node of the mouse while the image at the bottom end indicates an inguinal lymph node of the mouse.
Figure 11:
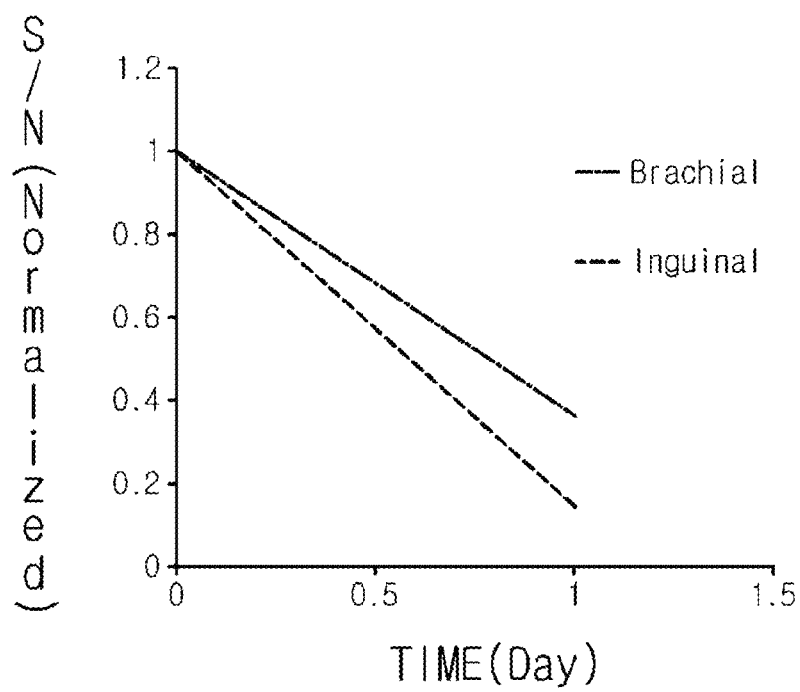
FIG. 11 illustrates a signal intensity of in vivo lymph node image of the mouse in Example 8-3 in a signal to noise ratio, specially, shows a variation in signal intensities of brachial and inguinal lymph nodes.

FIG. 10 illustrates in vivo MRI lymph node contrast image obtained using nanoparticles of 7 nm iron oxide modified by glucose 6-phosphate ethanolamine derivative. From the figure, it can be seen that a normal lymph node of a mouse had iron oxide uptake 1 day after injection, thus turning dark. FIG. 11 shows a decrease in signal intensity according to Equation 2, demonstrating considerable decrease in signal intensity.

Example 9

In Vivo MRI Image Formation with Composition Including 10 nm Core Iron Oxide Hydrophilized Using Glucose 6-Phosphate Polyethyleneglycol Using monosaccharide-phosphate-polyethyleneglycol prepared by the methods described in Example 4 and 5, 10 nm core iron oxide was hydrophilized to prepare colloids having a number mean hydrodynamic diameter of 30 nm. According to the same procedure described in Example 8-3, T2 contrast imaging performance for mouse lymph nodes was tested, thus obtaining images of the lymph nodes before and after injection of the contrast agent.

For colloidal solutions of iron oxide nanoparticles surface-modified using a glucose 6-phosphate polyethyleneglycol, hydrodynamic diameters are listed in Table 3.

TABLE 3

| Core size | Vol. mean (nm) | No. mean (nm) |
|---|---|---|
| 3 nm | 19 | 14 |
| 10 nm | 96 | 26 |

Figure 12:
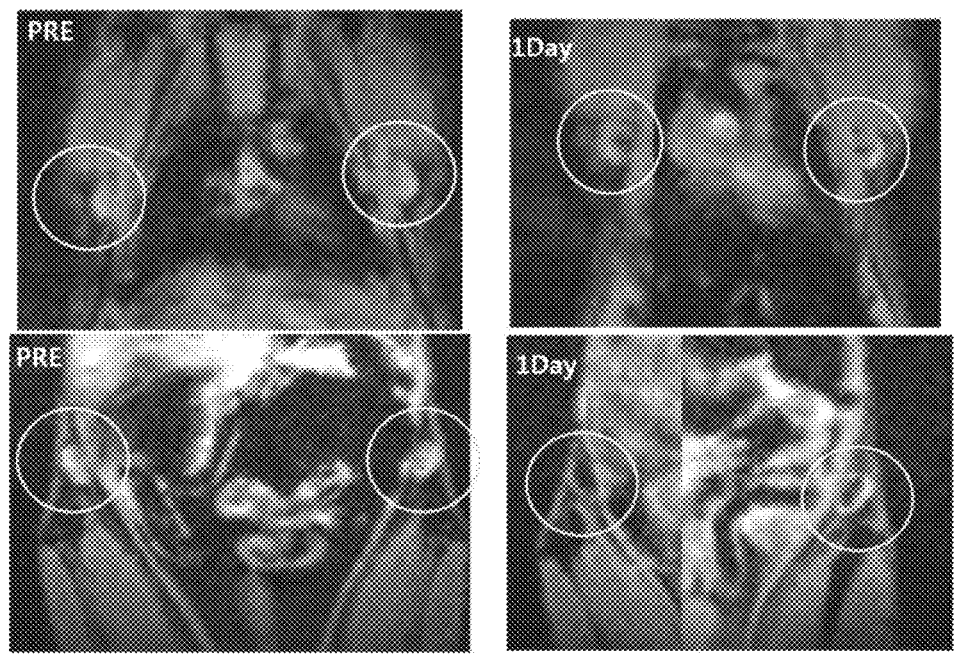
FIG. 12 is in vivo MRI lymph node contrast image of a mouse in Example 9, wherein images before injection (PRE) and 1 day after injection (1 Day) are included, and the image at the upper side indicates a brachial lymph node of the mouse while the image at the lower side indicates an inguinal lymph node of the mouse.
Figure 13:
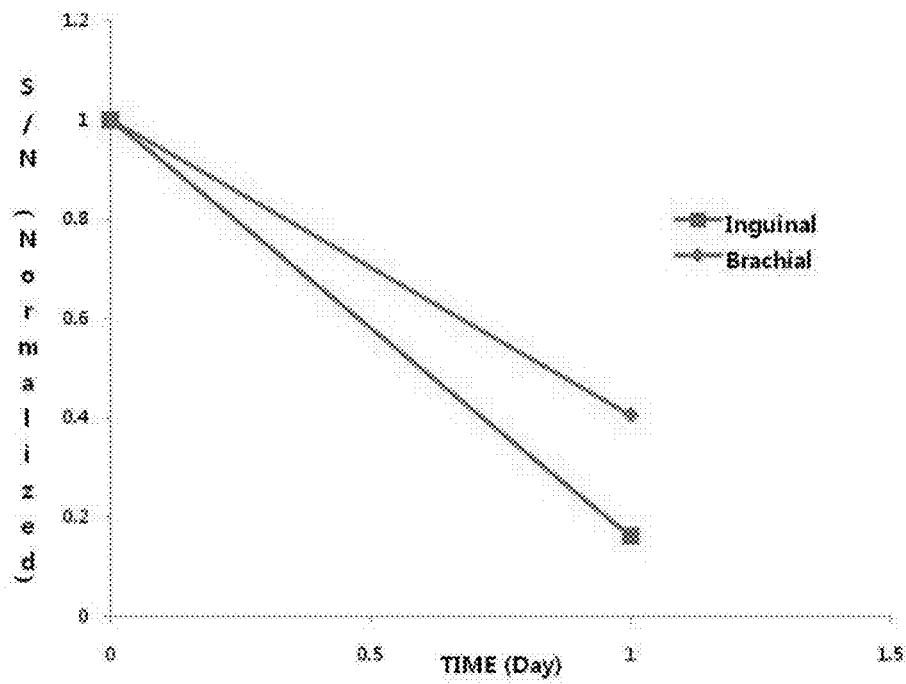
FIG. 13 illustrates a signal intensity of in vivo lymph image of the mouse in Example 9 in a signal to noise ratio, specially, shows a variation in signal intensities of brachial and inguinal lymph nodes.

FIG. 12 illustrates in vivo MRI lymph node contrast image obtained using nanoparticles of 10 nm iron oxide modified by glucose 6-phosphate polyethyleneglycol. From the figure, it can be seen that a normal lymph node had iron oxide uptake 1 day after injection, thus turning dark. FIG. 13 shows a decrease in signal intensity according to Equation 2, demonstrating considerable decrease in signals.

Example 10

MR In Vitro Relaxation Characteristic of Composition Including Iron Oxide Nanoparticles Surface-Modified Using Monosaccharide Phosphate and a Derivative Thereof In order to determine MR contrast imaging ability of each of compositions including iron oxide nanoparticles hydrophilized by the methods described in Examples 1, 2 and 3, iron oxide nanoparticles having sizes of 2 nm, 3 nm, 7 nm, 10 nm and 20 nm, respectively, were subjected to phantom imaging using a gradient coil in 4.7 T MR scanner (Biospec 47/40, Bruker Biospin MRI GmbH), in order to evaluate relaxation performance. A concentration of iron oxide nanoparticles was measured through ICP-AES, T2 relaxation time was measured using MSME (Multi Slice-Multi Echo sequence) pulse sequence, and particular parameters are as follows.

T1 imaging parameters are as follows: RARE sequence, TR=100, 200, 500, 1,000, 2,000, 4,000, 6,000, 8,000 ms, TE=7,756 ms, FOV=5 cm, Matrix size=128×128, slice thickness=2 mm.

T2 imaging parameters are as follows:
Carr Purcell Meiboom Gill (CPMG) sequence, TR=ms, TE=7.5 960.0 ms, FOV=5 cm, Matrix size=128×128, slice thickness=2 mm.

MRI in vitro imaging results of iron oxide nanoparticles using a monosaccharide-phosphate are shown in Table 4.

TABLE 4

| core diameter | Material for hydrophilization | r1 ($mM^{-1}s^{-1}$) | r2 ($mM^{-1}s^{-1}$) | r2/r1 |
|---|---|---|---|---|
| 2 nm | PO-Glu | 1.3 | 1.7 | 1.3 |
| 3 nm | PO-Glu | 3.5 | 14.8 | 4.2 |
| 4 nm | PO-Glu | 2.8 | 20.0 | 7.0 |
| 7 nm | PO-Glu | 4.3 | 38.0 | 8.81 |
| 10 nm | PO-Glu | 3.3 | 82.4 | 24.4 |
| 20 nm | PO-Glu | 1.8 | 526 | 288 |
| 7 nm | PO-Man | 4.0 | 68.3 | 16.8 |
| 10 nm | PO-Man | 3.6 | 146 | 39.9 |
| 10 nm | PO-Fru | 4.1 | 127 | 30.8 |
| 3 nm | PO-Glu-EA | 3.3 | 26 | 7.8 |
| 7 nm | PO-Glu-EA | 2.5 | 41 | 16.4 |
| 3 nm | PO-Glu-PEG | 3.9 | 30 | 7.7 |
| 10 nm | PO-Glu-PEG | 2.6 | 130 | 50.6 |

*PO-Glu: Glucose 6-phosphate, PO-Man: Mannose 6-phosphate, PO-Fru: Fructose-6-phosphate, PO-Glu-EA: Glucose 6-phosphate ethanolamine derivative, PO-Glue-PEG: Glucose 6-phosphate PEG derivative Table 4 shows MRI relaxation performance of each of colloidal solutions of iron oxide nanoparticles surface-modified using a monosaccharide-phosphate and/or derivative thereof. Iron oxide nanoparticles having a small core size may be effectively used as a T1 contrast agent, since r1 value is not too small while r2 value is small. On the other hand, iron oxide nanoparticles having a large core size exhibit a much larger r2 value, thus being used as a T2 contrast agent. Accordingly, it was confirmed that iron oxide nanoparticles substituted with a monosaccharide-phosphate and a derivative thereof may be effectively used as T1 and/or T2 contrast agent.

Example 11

Toxicity Test of Colloidal Solution of Iron Oxide Nanoparticles Surface-Modified Using Glucose 6-Phosphate and Derivative Thereof In a toxicity test of iron oxide nanoparticle colloidal solution, MTT assay was conducted with Hep G2 cells. Three kinds of nanoparticles, that is, 10 nm core iron oxide nanoparticles hydrophilized using glucose 6-phosphate (A); 10 nm core iron oxide nanoparticles hydrophilized using a glucose 6-phosphate-PEG derivative (B); and 3 nm core iron oxide nanoparticles hydrophilized using glucose 6-phosphate-aminoalcohol (C) were dispersed, respectively, in a 5% DW solution. Then, each solution passed through a 0.2 µm sterile syringe filter. The filtered solution was subjected to measurement of a concentration by inductively coupled plasma-atomic emission spectroscopy (that is, ICP-AES). After measuring the concentration, 200 µl of fraction taken from each of the iron oxide nanoparticle colloidal solutions and mixed with 200 µl of a medium (DMEM: Dulbeco's Modified Eagle's Medium 89%, Pluronic® F-127 10%, AA: antibiotic-antimycotic 1%). Thereafter, the solution was diluted by ½ times, to prepare a total of nine (9) samples. As a control, 5% DW solution without iron oxide was prepared by the same procedures as described above. 100 µl of each sample was added to HepG2 cells proliferated by subculture, followed by incubation at 37° C. for 24 hours. Next, 20 µl of MTT (3-(4,5-dimethylthiazol-2-yl)-2,5-diphenyl-2H-tetrazolium bromide) reagent was added, followed by incubation at 37° C. for 4 hours. In order to dissolve formazan crystals generated during incubation, 100 µl of a soluble solution was added to the above material and incubation was additionally continued at 37° C. for 24 hours. After incubation, optical densities at 550 nm and 690 nm, respectively, were measured using a microplate reader (Molecular Devices Co., Spectra Max 190) and cell viability was calculated from the measured optical densities. The cell viability may be calculated according to the following Equation 3.

Cell viability (%)={[$OD_{i,550}-OD_{i,690}$]/[$ODS_{i,550}-ODS_{i,690}$]}×100     [Equation 3]

$OD_{i,550}$: Optical density at 550 nm of well plate No. i in which the sample is introduced.
$OD_{i,690}$: Optical density at 690 nm of well plate No. i in which the sample is introduced.
$ODS_{i,550}$: Optical density at 550 nm of control well plate No. i.
$ODS_{i,690}$: Optical density at 690 nm of control well plate No. i.

Figure 14:
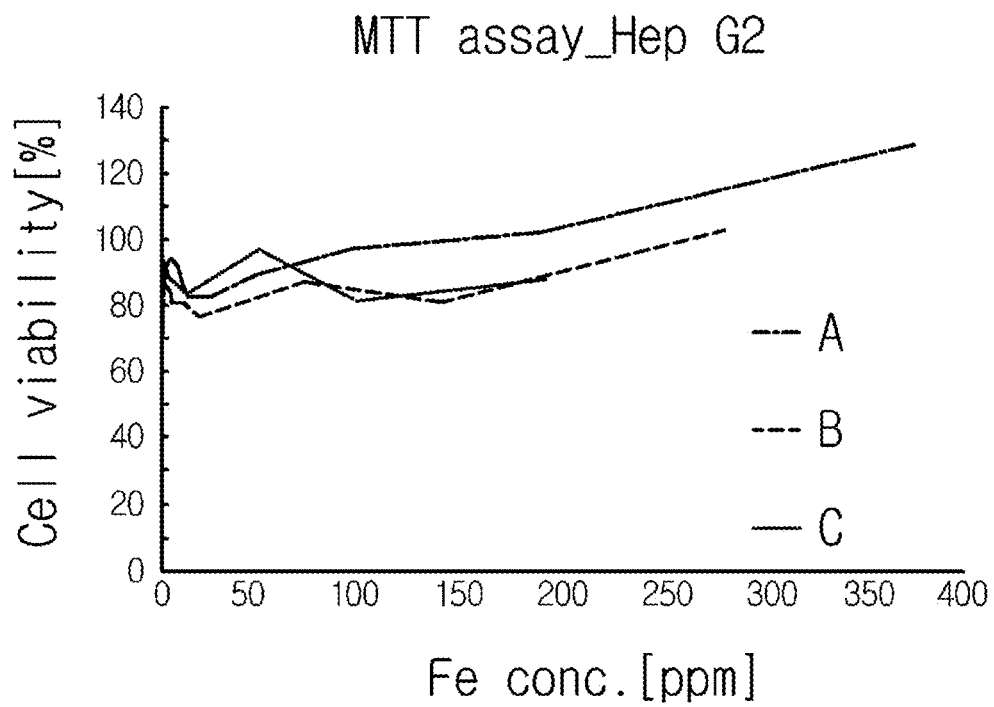
FIG. 14 illustrates MTT assay results of Example 11, wherein (A) 10 nm iron oxide nanoparticles stabilized by glucose 6-phosphate, (B) 10 nm iron oxide nanoparticles stabilized by glucose 6-phosphate-PEG derivatives, and (C) 3 nm iron oxide nanoparticles stabilized by glucose 6-phosphate-aminoalcohol.

FIG. 14 is graphs illustrating results of cell viability tests. In a cell viability test, an acceptable error range (commonly, tolerance) is generally ±20%. From results of the present test, it can be found that 80% or more of cell viability was exhibited at a concentration section to be tested. Especially, since cells show no abnormal condition even at a high concentration of 200 µg/mL, it may be considered that iron oxide nanoparticles have favorable biocompatibility.

Example 12

Preparation of Colloidal Solution of Nanoparticles Hydrophilized by Glucose 6-Phosphate Several kinds of nanoparticles stabilized with an organic surfactant were hydrophilized using glucose 6-phosphate by the same procedure described in Example 1, to prepare a colloidal solution having high dispersion stability. Results thereof are shown in Table 5.

TABLE 5

| Core nanoparticle | Size of core nanoparticle (nm) | Hydrodynamic diameter (No. mean) (nm) |
|---|---|---|
| MnO | 14 nm | 20 nm |
| ZnO | 20 nm | 25 nm |
| CdS | 6 nm | 10 nm |
| Au | 10 nm | 15 nm |
| $CoFe_2O_4$ | 12 nm | 15 nm |
| FePt | 10 nm | 13 nm |
| GdO | 25 nm | 30 nm |
| CdSe/CdS (core shell) | 8 nm | 12 nm |

Example 13

Hydrophilization of Nanoparticles Using Glucose 6-Phosphate in Various Solvents

Various polar solvents such as dimethylsulfoxide (DMSO) and ethanol having affinity to water were used instead of the solvent THF used in Example 1. Using glucose 6-phosphate, iron oxide nanoparticles having a size of 10 nm were hydrophilized, thus resulting in a colloidal solution having dispersion stability in water. Table 6 shows relative ratios of solvents used in hydrophilization experiments and DIW, reaction temperature, reaction time, hydrodynamic diameter after hydrophilization, etc.

Example 13-1

Preparation of Nanoparticle Colloidal Solution by Hydrophilization of 10 nm Iron Oxide Nanoparticles Using Glucose 6-Phosphate in DMSO A dispersion of 100 mg of iron oxide nanoparticles stabilized using oleic acid in 8 ml of DMSO, and another dispersion of 200 mg of glucose 6-phosphate sodium salt in 2 ml of DIW, were admixed and the mixture was agitated and reacted at 120° C. for 12 hours, followed by cooling and settling the same. After removal of DMSO, a hydrophilic composition was obtained. Adding distilled water to the composition, a colloidal solution of nanoparticles surface-substituted with glucose 6-phosphate having excellent dispersion stability in water was achieved.

Example 13-2

Hydrophilization of 10 nm Iron Oxide Nanoparticles Using Glucose 6-Phosphate in Ethanol After adding 100 mg of iron oxide nanoparticles stabilized using oleic acid to 8 ml of ethanol, a solution of 200 mg of glucose 6-phosphate sodium salt dispersed in 2 ml of DIW was mixed with the above nanoparticle solution and the mixture was agitated and reacted at 70° C. for 12 hours, followed by cooling and settling the same. After removal of ethanol, a hydrophilized nanoparticle composition was obtained. Adding distilled water to the composition, a colloidal solution of nanoparticles surface-substituted with glucose 6-phosphate having excellent dispersion stability in water was achieved.

TABLE 6

| Solvent | Solvent:water | Reaction temperature/ time | Hydrodynamic diameter (volume mean, nm) | Hydrodynamic diameter (number mean, nm) |
| --- | --- | --- | --- | --- |
| DMSO | 8:2 | 120° C./8 h | 26.9 | 11.9 |
| Ethanol | 8:2 | 70° C./8 h | 48.6 | 13.05 |

Example 14

Preparation of Iron Oxide Nanoparticle Colloidal Solution by Glucose 6-Phosphate Example 14-1

Modification of Hydrophobic Iron Oxide Nanoparticles to be Hydrophilic

According to Example 1 in Korean Patent Application No. 10-2011-0011294, hydrophobic iron oxide was modified to be hydrophilic. 50 mg of iron oxide ($Fe_3O_4$) with a size of 3 nm and oleic acid adhered on the surface thereof and sodium sulfate ($Na_2SO_4$, average particle size: 150 μm) were mixed in a ratio by weight of 1:500. The mixture was agitated in n-hexane and then evaporated hexane. By heating the mixture of iron oxide nanoparticles and sodium sulfate powder at 500° C. for 5 hours under atmosphere, oleic acid was removed. In order to remove the salt, the nanoparticles and salt powder were washed three times with distilled water. The product was identified to be hydrophilic by observing iron oxide nanoparticles dispersed in water. The agglomerated particles were not observed after heating. Although the prepared iron oxide nanoparticles are dispersed in water, they tend to settle to the bottom over time since a stabilizer is not present enough on the surface thereof.

As a result of measuring a hydrodynamic diameter of the nanoparticle composition in the colloidal solution using Malvern Zetasizer Nano ZS, it was found that the hydrodynamic diameter is 30 nm and the reason of this is to be considered that particles are agglomerated to one another in an aqueous solution since a surface stabilizer is not present.

Example 14-2

Stabilization of the Modified Iron Oxide Nanoparticles Using Glucose 6-Phosphate 1 g of glucose 6-phosphate sodium salt was added to an aqueous solution (10 ml) of iron oxide nanoparticles prepared in Example 14-1 and maintained at 60° C. for 4 hours under sonication. After completing the reaction, it can be seen that a colloidal solution of iron oxide nanoparticles attached with glucose 6-phosphate were prepared. Turbidity did not change after leaving for 6 months at room temperature, which demonstrated excellent long term stability of colloids. As a result of measuring a hydrodynamic diameter of the nanoparticle composition in the colloidal solution using Malvern Zetasizer Nano ZS, it was found that the hydrodynamic diameter is 8.5 nm. Therefore, compared to iron oxide nanoparticles prepared in Example 14-1, it can be confirmed that the hydrodynamic diameter is decreased while having improved dispersion stability.

Comparative Example 1

Preparation of Hydrophilized Capsule of Iron Oxide Nanoparticles 40 mg of iron oxide nanoparticles having a size of 10 nm stabilized with oleic acid, as well as 40 mg of poly(lactic-co-glycolic acid) (PLGA), were dispersed in an ethyl acetate solution. Then, the dispersion was mixed with 4 ml of Pluronic® F127 solution (BASF Corporation, difunctional block copolymer), followed by agitation, resulting in capsules. Measuring results of a hydrodynamic diameter of the capsules are shown in Table 1.

Comparative Example 2

Hydrophilization of Iron Oxide Nanoparticles Using PO-PEGs 50 mg of iron oxide nanoparticles having a size of 3 nm stabilized with oleic acid, as well as 5 g of PO-PEGs (PEG, MW: 2000), were provided in 10 ml of ethanol, followed by agitation at 70° C. for 12 hours, resulting in hydrophilic iron oxide nanoparticles. Measuring results of a hydrodynamic diameter of the nanoparticles are shown in Table 1.

As set forth above, specific technical configurations and embodiments of the present invention have been described according to the foregoing examples and accompanying drawings, however, such examples are provided for illustrative purpose to more clearly understand the present invention and the scope of the present invention is not particularly limited thereto. Therefore, it will be apparent to those skilled in the art that various modifications and alterations can be made from the foregoing description.

Accordingly, the spirit of the present invention is not particularly restricted to the exemplary embodiments described above and the scope of the present invention may include not only the subject matters defined by the appended claims but also modification and equivalents thereof.

The invention claimed is:

1. Iron oxide nanoparticles surface-modified by adhering a monosaccharide-phosphate derivative of Formula 2 on the surface of iron oxide nanoparticles

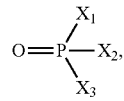

Formula 2 wherein $X_1$ is a monosaccharide, $X_2$ is aminoalcohol, and $X_3$ is OH; and wherein a core size of the iron oxide nanoparticles ranges from 1 nm to 20 nm and a difference between a number mean hydrodynamic diameter and a core size of iron oxide nanoparticles is 6 nm or less.

2. The nanoparticles of claim 1, wherein the aminoalcohol is one or two or more selected from a group consisting of ethanolamine, heptaminol, isoetharine, norepinephrine, propanolamine and sphingosine.

3. The nanoparticles of claim 1, wherein the iron oxide is one or two or more selected from a group consisting of FeO, $Fe_3O_4$ (magnetite), $\alpha$-$Fe_2O_3$, $\beta$-$Fe_2O_3$, $\gamma$-$Fe_2O_3$ (maghemite), $\epsilon$-$Fe_2O_3$, $Fe(OH)_2$, $Fe(OH)_3$, $\alpha$-FeOOH, $\beta$-FeOOH, $\gamma$-FeOOH, $\delta$-FeOOH, $Fe_5HO_8 \cdot 4H_2O$, $5Fe_2O_3 \cdot 9H_2O$, $FeOOH \cdot 4H_2O$, $Fe_8O_8(OH)_6(SO) \cdot nH_2O$, $Fe^{3+}_{16}O_{16}(OH.SO_4)_{12-13} \cdot 10\text{-}12H_2O$ and a mixture of $Fe_3O_4$ (magnetite) and $\gamma$-$Fe_2O_3$ (maghemite).

4. The nanoparticles of claim 1, wherein the iron oxide is one or two or more selected from a group consisting of $Fe_3O_4$ (magnetite), $\gamma$-$Fe_2O_3$ (maghemite) and a mixture thereof.

5. The nanoparticles of claim 1, wherein the surface-modified iron oxide nanoparticles are obtained by contacting a solution of a monosaccharide-phosphate of Formula 1 or a monosaccharide-phosphate derivative of Formula 2 dispersed in water with iron oxide nanoparticles having a lipophilic ligand bonded to the surface thereof, and a polar solvent, to modify the surface of the iron oxide nanoparticles into a hydrophilic state.

6. A colloidal solution prepared by dispersing the nanoparticles of claim 1 in water.

7. A contrast agent including the colloidal solution of claim 6.

8. The contrast agent of claim 7, wherein the contrast agent is a magnetic resonance imaging (MRI) T1 contrast agent or T2 contrast agent.

9. A method for manufacturing surface-modified hydrophilic iron oxide nanoparticles, comprising contacting: a solution of a monosaccharide-phosphate derivative of Formula 2 dispersed in water; a polar organic solvent; and iron oxide nanoparticles having a lipophilic ligand bonded to the surface thereof, to modify the surface of the iron oxide nanoparticles into a hydrophilic state,

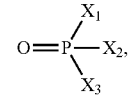

Formula 2 wherein $X_1$ is a monosaccharide, $X_2$ is aminoalcohol, and $X_3$ is OH; and wherein a core size of the surface-modified iron oxide nanoparticles ranges from 1 nm to 20 nm and a difference between a number mean hydrodynamic diameter and a core size of the surface-modified iron oxide nanoparticles is 6 nm or less.

10. The method of claim 9, wherein the iron oxide is one or two or more selected from a group consisting of $Fe_3O_4$ (magnetite), $\gamma$-$Fe_2O_3$ (maghemite) and a mixture thereof.

* * * * *